Figure 1A:
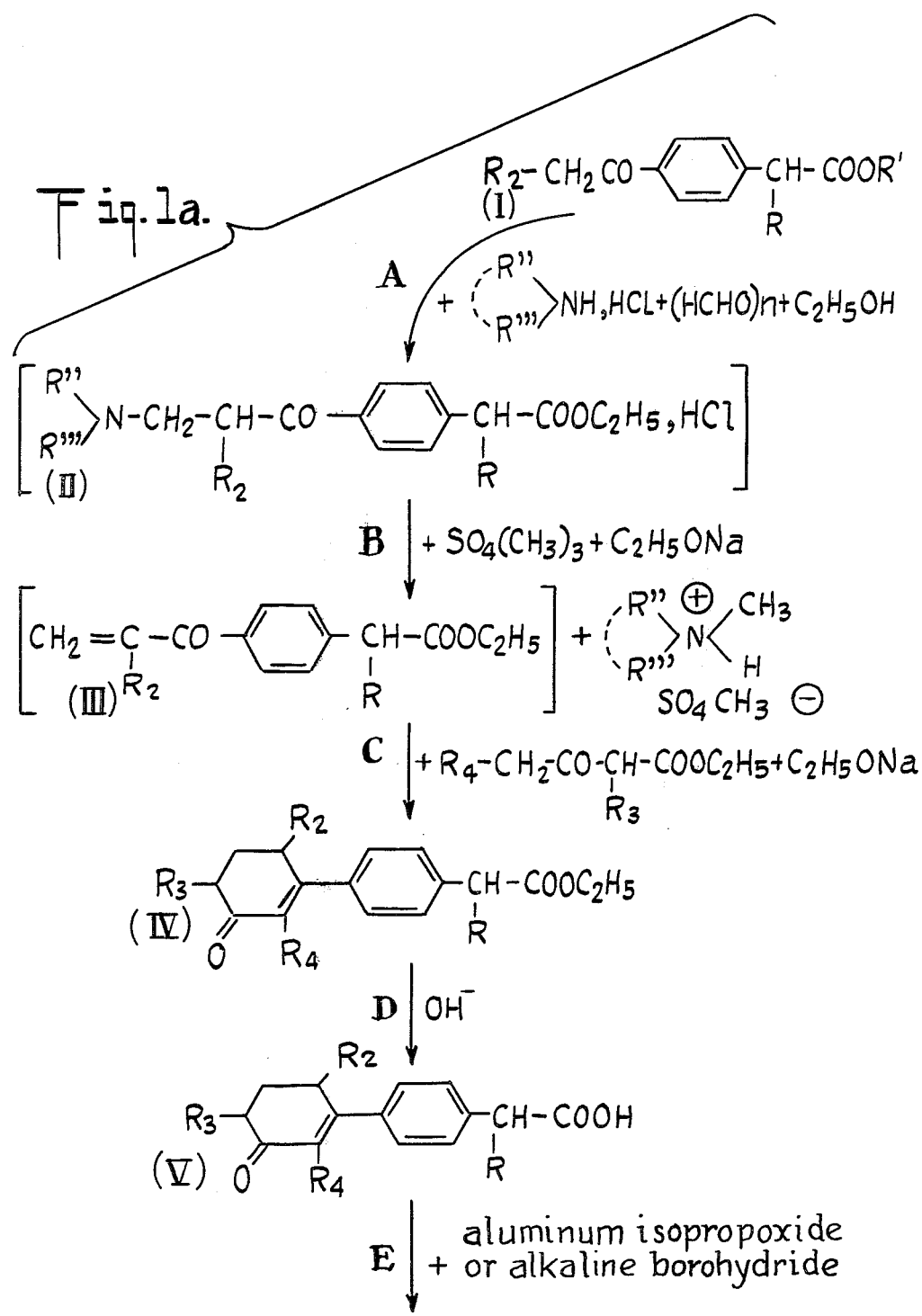

United States Patent [19]

Maillard

[11] 4,181,736

[45] Jan. 1, 1980

[54] PHENYLACETIC ACID DERIVATIVES AND THERAPEUTIC COMPOSITION CONTAINING SAME

[75] Inventor: Jacques G. Maillard, Paris, France

[73] Assignee: Laboratoires Jacques Logeais, Moulineaux, France

[21] Appl. No.: 962,653

[22] Filed: Nov. 21, 1978

Related U.S. Application Data

[63] Continuation of Ser. No. 749,479, Dec. 10, 1976, abandoned, which is a continuation of Ser. No. 285,127, Aug. 31, 1972, Pat. No. 4,031,133.

[30] Foreign Application Priority Data

Sep. 4, 1971 [GB] United Kingdom ............... 41327/71

[51] Int. Cl.$^2$ ...................... A61K 31/19; C07C 65/20; C07C 69/95
[52] U.S. Cl. ...................... 424/317; 560/51; 562/459
[58] Field of Search ............ 560/51; 562/459; 424/317

[56] References Cited

U.S. PATENT DOCUMENTS

| | | | |
|---|---|---|---|
| 3,457,300 | 7/1969 | Dorn | 560/51 |
| 3,772,343 | 11/1973 | Noguchi | 560/51 |
| 3,822,309 | 7/1974 | Rossi | 560/51 |

*Primary Examiner*—Jane S. Myers

*Attorney, Agent, or Firm*—Cooper, Dunham, Clark, Griffin & Moran

[57] ABSTRACT

This invention relates to phenylacetic acid derivatives having the formula:

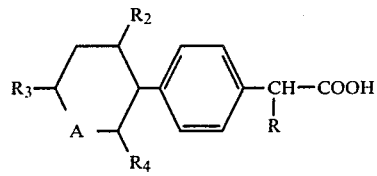

in which A represents a grouping

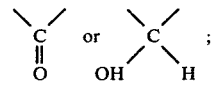

$R$, $R_2$, $R_3$ and $R_4$, which may be the same or different, represent each hydrogen or an alkyl group, and represents a single or double carbon-carbon bond; and their salts with inorganic and organic bases. Said compounds possess anti-inflammatory and analgesic activities that make them therapeutically useful, in particular for the treatment of rheumatic diseases and of local inflammations.

6 Claims, 2 Drawing Figures

PHENYLACETIC ACID DERIVATIVES AND THERAPEUTIC COMPOSITION CONTAINING SAME

This is a continuation, of application Ser. No. 749,479 filed Dec. 10, 1976, now abandoned, which is in turn a continuation of application Ser. No. 285,127 filed Aug. 31, 1972 which is now U.S. Pat. No. 4,031,133.

This invention relates to new phenylacetic acid derivatives having useful pharmacological properties, to a process for their preparation and to a therapeutic composition containing same as active ingredient.

The new derivatives of this invention have the general formula

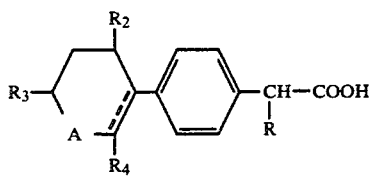

in which A represents grouping

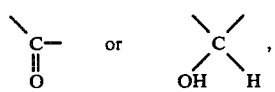

$R_1$, $R_2$, $R_3$ and $R_4$, which may be the same or different, represent each hydrogen or an alkyl group (having in particular from 1 to 4 atom carbons for R and $R_3$ and from 1 to 8 carbon atoms for $R_2$ and $R_4$), and ⇌ represents a single or double carbon-carbon bond.

The invention includes also within its scope the salts of acids of the formula (X) with inorganic (typically sodium and potassium hydroxide) or organic (amines) bases and which may be prepared from the acids by well known conventional methods.

The invention relates also to a process for the preparation of derivatives having the formula (X) described above, comprising:

(a) reacting a compound of the formula:

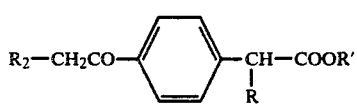

in which R and $R_2$ have the above-defined meanings and R' is hydrogen or a lower alkyl residue, with formaldehyde and a secondary amine hydrochloride in alcoholic medium;

(b) reacting the resulting amino-ester, in the presence of an alkali metal alkoxide, with an alkyl sulfate and a keto-ester having the formula:

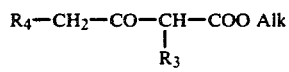

in which $R_3$ and $R_4$ have the above-defined meanings and Alk is a lower alkyl residue, to give an ester having the formula

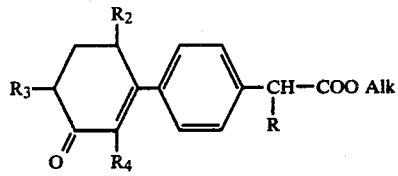

(c) saponifying the ester having the formula (IV) to give the corresponding acid having the formula:

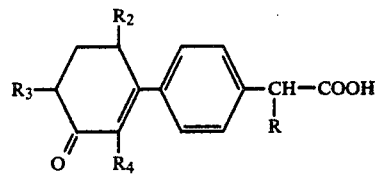

(d) optionally reducing said acid to give the compound of the formula:

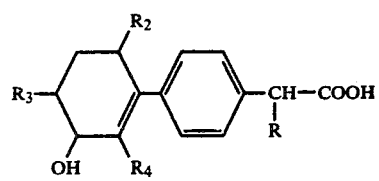

and optionally (e) hydrogenating the compound of the formula (VI) to give the compound having the formula:

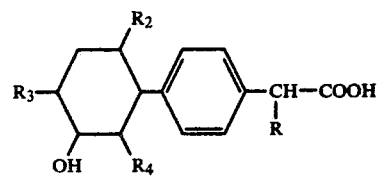

and optionally (f) oxidizing the compound having the formula (VII) to give the compound having the formula:

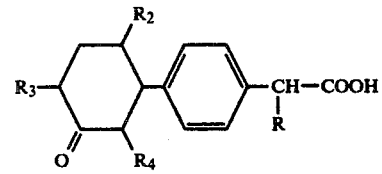

Figure 1B:
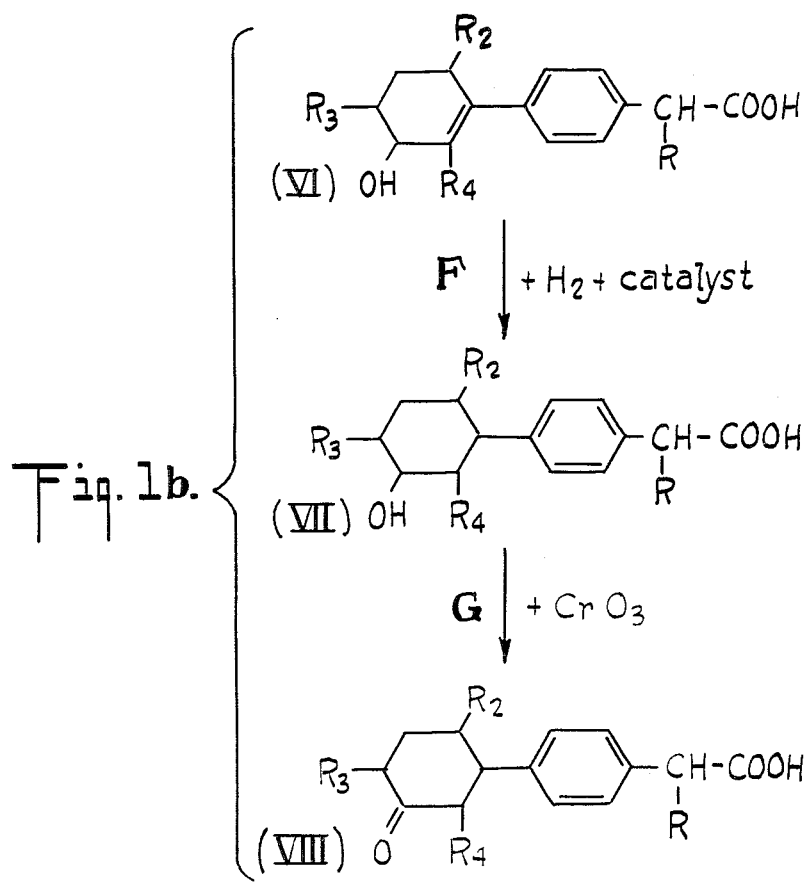

The method of the invention for the preparation of compounds of the formula (X) comprises typically the reaction sequence illustrated for exemplary purposes in FIGS. 1a and 1b of the accompanying drawing.

Reaction A comprises reacting the starting derivatives of the formula (I) in which R' is hydrogen or an alkyl (particularly ethyl) group with formaldehyde or a formaldehyde polymer (trioxymethylene) and a secondary amine hydrochloride such as piperidine, dimethylamine or morpholine hydrochloride, within a boiling alcohol (particularly ethanol), according to the technique described in Organic Reactions, Vol. I, page 329. In the formula of the amine, R" and R''' represent each an alkyl group or, together with the nitrogen atom to which they are attached, form a heterocycle which may contain another heteroatom. Reaction A may also be carried out within acetic acid.

When an acid (R'=H) is used as starting material, this acid is esterified in the course of the reaction, at the expense of the alcohol used as solvent, and in all cases the ester of the formula (II) is obtained as the hydrochloride. The crude product is used as such for the subsequent reactions.

The compounds of the formula (I) used as starting materials are described by D. PAPA et al. (J.Amer.-Chem.Soc., 1946, 68, 2133) in the case where R=R$_2$=H and R'=H or C$_2$H$_5$. Thus, they are obtained by acetylation of ethyl phenylacetate, followed or not by saponification of the ester. Similarly, the derivatives of the formula (I) in which R=H or alkyl, R$_2$=H or alkyl and R'=H or C$_2$H$_5$ are obtained by acylation of a phenylacetic acid or ester alkylated or not with R at α-position.

Reactions B and C and conducted in a single operation, the intermediately formed product having the formula (III) being not isolated. In practice, the crude ester of the formula (II) is dissolved in ethanol containing one equivalent of sodium ethoxide, treated at low temperatures (from −5° to +5° C.) with an ethanol solution of ethyl acetoacetate (R$_3$=R$_4$=H) or of an homologous keto-ester (R$_3$ and/or R$_4$=alkyl), sodated by means of a second equivalent of sodium ethoxide. Methyl sulfate is added to the mixture at low temperature, and the ester of the formula (IV) is isolated by the usual methods.

During reaction D, the ester of the formula (IV) is saponified by boiling with an alkali metal carbonate in aqueous-alcoholic solution. The acids of the formula (V) are isolated by acidification and purified by crystallization or distillation. Said reaction D may also be conducted in the cold, by means of an aqueous-alcoholic solution of sodium or potassium hydroxide.

The ketonic acids of the formula (V) may be reduced to hydroxyl derivatives of the formula (VI) (reaction E) either with an alkali metal borohydride in aqueous or aqueous-alcoholic solution, or with boiling aluminum isopropoxide in isopropanol, under the usual conditions of the Meerwein-Poondorfreaction (Org. Reactions, Vol. II, page 178).

The acids of the formula (VII) are obtained by catalytic hydrogenation of acids of the formula (VI), in the presence of palladium or of platinum oxide (Reaction F). They may also be prepared directly from the acids of the formula (V) by catalytic hydrogenation of the double bond and simultaneous reduction of the CO grouping in the presence of platinum oxide.

The acids of the formula (VIII) are prepared from acids of the formula (VII) (Reaction G), by oxidation of the OH grouping to the ketone, using an alkali metal bichromate in acidic medium.

The derivatives having the formulae (V), (VI), (VII) and (VIII) are derivatives according to the invention which are all included within the scope of aforementioned general formula (X).

The esters of the formula (IV) are new chemical compounds and, as such, constitute a further feature of the present invention.

The non-limiting examples which follow are given to illustrate the process and the derivatives of the invention.

EXAMPLE 1

4-(3'-Oxo-1'-cyclohexenyl)phenylacetic acid (Formula V: R=R$_2$=R$_3$=R$_4$=H)

(A) 54 g (0.26 mole) ethyl 4-acetyl phenylacetate (formula I: R=R$_2$=H; R'=C$_2$H$_5$) are dissolved in 75 ml ethanol with 31 g (0.26 mole) piperidine hydrochloride, 10 g (0.33 mole) trioxymethylene and a few drops of concentrated HCl. The solution is heated to boiling during one hour, and then during two hours after a further addition of trioxymethylene (7.2 g). After evaporation of the ethanol, the residue is taken up into acetone, filtered and evaporated to dryness. The resulting residue of hydrochloride of the ester of the formula (II) is used as such for the subsequent reactions. (Weight: 59 g; 0.174 mole. Yield: 67%).

(B–C). To a sodium ethoxide solution prepared from 2.7 g (0.117 g-atom) sodium in 65 ml ethanol, are added 18.5 ml (19 g; 0.14 mole) ethyl acetoacetate and then, at 5° C. 16 g (0.047 mole) of the hydrochloride of the ester of the formula (II) (R=R$_2$=H). While cooling to about 3° C., 10.7 ml (0.11 mole) methyl sulfate are added dropwise over forty-five minutes, and the reaction mixture is then stirred during eighteen hours at room temperature. The alcohol is evaporated off and the residue is taken up into water and extracted with ether. Evaporation of the ether leaves an oily residue consisting of the ester of the formula (IV) (R=R$_2$=R$_3$=R$_4$=H).

(D). The above ester of the formula (IV) is heated to boiling during twenty-four hours with 110 ml of 10% aqueous sodium carbonate solution and 40 ml of ethanol. The alcohol is then evaporated off and the aqueous solution is washed with ether and made acidic, giving 9 g of precipitate of the acid of the formula (V) (R=R$_2$=R$_3$=R$_4$=H). M.p.=125° C. Overall yield: 85%.

Analysis: C$_{14}$H$_{14}$O$_3$: Calculated %: C=73.02; H=6.13. Found %: C=72.8; H=6.4

EXAMPLE 2

2-[4-(3'-Oxo-1'-cyclohexenyl)-phenyl]propionic acid (Formula V: R=CH$_3$; R$_2$=R$_3$=R$_4$=H)

(A). This step is conducted, as in Example 1, from 10 g (0.052 mole) 2-(4-acetyl-phenyl)-propionic acid (Formula I: R=CH$_3$; R$_2$=H; R'=H), piperidine hydrochloride and trioxymethylene, within boiling ethanol. The hydrochloride of the corresponding ester of the formula (II) formed at the expense of the ethanol used as solvent is isolated on completion of the reaction.

(B–C). Said steps are conducted, as in Example 1, by action of the hydrochloride of the ester of the formula (II) (R=CH$_3$; R$_2$=H) on sodium ethylacetoacetate, in the presence of excess sodium ethoxide and methyl sulfate, by cooling to about 5° C. and then at room temperature. The ester of the formula (IV) (R=CH$_3$; R$_2$=R$_3$=R$_4$=H) is isolated in the usual manner.

(D). The above ester of the formula (IV) is saponified as in Example 1 with sodium carbonate in aqueous-alcoholic solution, and the acid is obtained as an oil which crystallizes on trituration with isopropyl oxide. Weight: 5 g. M.p.=127° C. Overall yield: 40%.

Analysis: C$_{15}$H$_{16}$O$_3$: Calculated %: C=73.75; H=6.60. Found %: C=73.45; H=6.35.

EXAMPLE 3

4-(3'-Hydroxy-1'-cyclohexenyl)-phenylacetic acid (Formula VI: $R=R_2=R_3=R_4=H$)

0.5 g (2.17 moles) of the acid having the formula (V) described in Example 1 are dissolved in 10 ml water, as the sodium salt, by addition of sodium hydroxide. Sodium borohydride (0.4 g; 10.6 moles) is added thereto over one hour, while stirring at 5° C. After stirring during a further hour and acidification with HCl, the precipitate is filtered off, washed, dried, and washed with chloroform. Weight: 0.2 g (40%). M.p.=148° C.

Analysis: $C_{14}H_{16}O_3$: Calculated %: C=72.39; H=6.94. Found %: C=72.15; H=7.30.

The same product may also be obtained by the following method;

2.3 g (10 moles) of the acid of the formula (V) described in Example 1 are dissolved in 20 ml isopropanol containing 4 g (20 mmoles) aluminum isopropoxide. The mixture is refluxed while removing the acetone formed in the reaction, and by following this removal by reaction of the distillate with dinitrophenylhydrazine (duration of the reaction: one hour and forty-five minutes). The alcohol is evaporated in vacuo, the residue is acidified with 1 N HCl and the insoluble portion is filtered, purified by conversion to the sodium salt with $NaCO_3H$ and reacidification, and is finally washed with chloroform. Weight: 1.1 g (50%). M.p.=149° C.

EXAMPLE 4

4-(3'-Hydroxy-cyclohexyl)-phenylacetic acid (Formula VII: $R=R_2=R_3=R_4=H$)

2 g of the acid of the formula (VI) described in Example 3 are dissolved in 30 ml ethanol and hydrogenated at normal pressure and at room temperature, in the presence of 5% palladium on charcoal (0.2 g). After absorption of the theoretical amount of hydrogen and filtration of the catalyst, the alcohol is evaporated and the residue is crystallized from chloroform. Weight: 1.5 g (75%). M.p.=173° C.

Analysis: $C_{14}H_{18}O_3$: Calculated %: C=71.77; H=7.74. Found %: C=71.50; H=7.65.

The same product may be obtained by hydrogenation of the acid of the formula (V) described in Example 1, within ethanol, in the presence of platinum oxide.

EXAMPLE 5

4-(3'-Oxo-cyclohexyl)-phenylacetic acid (Formula VIII: $R=R_2=R_3=R_4=H$)

To 0.5 g of the acid of the formula (VII) described in Example 4, in 5 ml ether, are added, between 0° and 5° C., 1.5 ml. of a solution, cooled at 0° C., of chromic acid (prepared from 9.7 g potassium bichromate, 30 ml water, 7.4 ml concentrated sulfuric acid and brought up to a volume of 50 ml). After stirring during a few minutes, another 1.5 ml of chromic acid solution are added thereto, the reaction mixture is stirred during five minutes, after which the aqueous phase is decanted and extracted with ether. The ether extract is washed with water, dried and evaporated, and the oily residue is distilled under reduced pressure. Weight: 0.5 g (100%). The product is crystallized from cyclohexane. M.p.=96° C.

Analysis: $C_{14}H_{16}O_3$: Calculated %: C=72.39; H=6.94. Found %: C=72.23; H=6.82.

EXAMPLE 6

2-[4-(3'-Hydroxy-1'-cyclohexenyl)-phenyl]propionic acid (Formula VI: $R=CH_3$; $R_2=R_3=R_4=H$)

This acid is obtained from the acid of the formula (V) described in Example 2, by reduction with sodium borohydride, according to the method described in Example 3. The acid is recrystallized from ethyl acetate. Yield: 80%. M.p.=140° C.

Analysis: $C_{15}H_{18}O_3$: Calculated %: C=73.15; H=7.37. Found %: C=73.25; H=7.28.

EXAMPLE 7

2-[4-(3'-Hydroxy-cyclohexyl)-phenyl]-propionic acid (Formula VII: $R=CH_3$; $R_2=R_3=R_4=H$)

2.44 g (10 mmoles) of the derivative of the formula (V) described in Example 2 are dissolved in 30 ml water, by addition of sodium hydroxide, at pH 6, and are then hydrogenated at room temperature and under ordinary pressure, in the presence of 5% palladium over charcoal (0.5 g). The theoretical amount of hydrogen is taken up after 3 hours. The filtered solution is made acidic. The oily precipitate is boiled with 30 ml cyclohexane which is decanted boiling and the residual oil is crystallized from isopropyl oxide, and then from benzene and finally from dichloroethane. Yield: 30%. M.p.=133°-143° C. (mixture of cis and transisomers).

Analysis: $C_{15}H_{20}O_3$: Calculated %: C=72.55; H=8.12. Found %: C=72.56; H=8.31.

The same product is obtained with a yield of 87%, by hydrogenation of the derivative of the formula (V) described in Example 2, in aqueous solution of the sodium salt, in the presence of $PtO_2$, or in ethanol or methanol solution with $PtO_2$ as catalyst.

EXAMPLE 8

2-[3'-Oxo-cyclohexyl)-phenyl]-propionic acid (Formula VIII: $R=CH_3$; $R_2=R_3=R_4=H$)

This acid is obtained by oxidation of the acid of the formula (VII) described in Example 7, according to the method described in Example 5. The crude material is converted to the semicarbazone, and is then regenerated by hydrolysis with 5 N HCl during 2 hours. The product is crystallized from cyclohexane. Yield: 56%. M.p. (tube)=88°-90° C.

Analysis: $C_{15}H_{18}O_3$: Calculated %: C=73.15; H=7.37. Found %: C=73.0; H=7.60.

EXAMPLE 9

4-(2'-Methyl-3'-oxo-1'-cyclohexenyl)-phenylacetic acid (Formula V: $R=R_2=R_3=H$; $R_4=CH_3$)

(A). This step is conducted according to the procedure used in Example 1.

(B-C). 11 g (0.076 mole) of ethyl propionylacetate are converted to the sodium derivative with sodium ethoxide in ethanol (500 ml). At +5° C., 26 g (0.076 mole) of the ester of the formula (II) described in step (A) of Example 1 are added, followed by 16 ml methyl sulfate. After one hour at 5° C., and 20 hours at room temperature, the ethanol is evaporated off and the residue is taken up into water and ether. The ether phase and the ether washings are combined, washed at pH 5 and concentrated. The ester of the formula (IV) is obtained as an oily residue.

(D). This oil is saponified by boiling with 110 ml of 10% aqueous $Na_2CO_3$ solution and 40 ml ethanol. After evaporation of the ethanol, redissolution in water and decolorizing over charcoal, the acid is precipitated by acidification, purified by conversion to the sodium salt which is washed with methanol and then with ethanol. Acidification gives the acid which crystallizes from ethyl acetate. Yield: 10%. M.p. = 126° C.

Analysis: $C_{15}H_{16}O_3$: Calculated %: C=73.75; H=6.60. Found %: C=73.93; H=6.80.

EXAMPLE 10

4-(4'-Methyl-3'-oxo-1'-cyclohexenyl)-phenylacetic acid (Formula V: $R=R_2=R_4=H$; $R_3=CH_3$)

(A). This step is conducted using the procedure of Example 1.

(B-C). 11 g (0.076 mole) of ethyl α-methyl-acetoacetate are treated as in Example 9, and converted to the ester of the formula (IV), obtained as an oil.

(D). This oil is saponified, as in Example 9, and the crude acid obtained by acidification is crystallized from ethyl acetate. Yield: 50%. M.p. = 134° C.

Analysis: $C_{15}H_{16}O_3$: Calculated %: C=73.75; H=6.60. Found %: C=73.50; H=6.48.

EXAMPLE 11

2-[4-(2'-Methyl-3'-oxo-1'-cyclohexenyl)-phenyl]-propionic acid (Formula V: $R=R_4=CH_3$; $R_2=R_3=H$)

(A). This step is conducted according to the procedure used in Example 2.

(B-C). 31.5 g (0.21 mole) of ethyl propionylacetate are converted to the sodium derivative with sodium ethoxide and are condensed with 30.2 g (0.085 mole) of the ester of the formula (II) described in Example 2. After the usual treatment, the ester of the formula (IV) is obtained as an oil.

(D). The crude ester is saponified by boiling with 150 ml of 10% aqueous $Na_2CO_3$ solution and 60 ml ethanol. After evaporation of the ethanol and filtration, acidification gives an oily acid which is extracted with ethyl acetate. Evaporation of the solvent leaves a residue which crystallizes from a water-methanol mixture. Yield: 33%. M.p. = 124°–125° C.

Analysis: $C_{16}H_{18}O_3$: Calculated %: C=74.39; C=7.02. Found %: C=74.39; C=7.24.

EXAMPLE 12

2-[4-(2'-Ethyl-3'-oxo-1'-cyclohexenyl)-phenyl]-propionic acid (Formula V: $R=CH_3$; $R_2=R_3=H$; $R_4=C_2H_5$)

(A). This step is conducted according to the procedure used in Example 2.

(B-C). Ethyl butyrylacetate, converted to the sodium derivative by means of sodium ethoxide, is condensed with the ester having the formula (II) described in Example 2. After the usual treatment, the ester of the formula (IV) is obtained as an oil.

(D). The crude ester is dissolved in ethanol and saponified by boiling with a 10% aqueous $Na_2CO_3$ solution, as in the preceding Example. The sodium salt is purified by dissolution in methanol, and then in ethanol which remove successively an insoluble mineral. The acid released is extracted with ethyl acetate and is then crystallized. M.p. = 120° C.

Analysis: $C_{17}H_{20}O_3$: Calculated %: M.W. = 272. Found (acidimetry) 275.

EXAMPLE 13

2-[4-(6'-Methyl-3'-oxo-1'-cyclohexenyl)-phenyl]-propionic acid (Formula V: $R_3=R_4=H$; $R=R_2=CH_3$)

(A). 25 g (0.107 mole) ethyl 2-(4-propionyl-phenyl)-propionate are dissolved in 50 ml acetic acid with 12.9 g (0.107 mole) piperidine hydrochloride, 4.8 g (0.16 mole) trioxymethylene and 0.1 ml concentrated HCl. After 30 minutes at 90° C., the acetic acid is distilled and the residue is taken up into water and ether. The aqueous phase is separated, made alkaline and extracted with ether. The latter is dried over $K_2CO_3$ and an anhydrous ether solution of HCl is added thereto. The resulting material is suction filtered, to give 32 g (81%) of hydrochloride of the ester of the formula (II). M.p. = 148° C.

(B-C). The hydrochloride of the ester of the formula (II) (0.087 mole) is added to an ethanol solution of sodium ethyl acetoacetate (0.218 mole) and is treated with methyl sulfate, as in the preceding examples. The reaction is completed by standing 17 hours at 20° C. and by refluxing during 4 hours. The crude ester of the formula (IV) is obtained by evaporation of the ethanol, extraction with ether and washing with water.

(D). The crude ester of the formula (IV) is saponified with a 10% aqueous $Na_2CO_3$ solution, as in the preceding examples. The acidification product of the sodium salt is extracted successively with ethyl acetate followed by isopropyl oxide, and is then purified by chromatography over alumina, to give 7 g (26%) of amorphous material characterized by its I.R. and U.V. spectra.

Analysis: $C_{16}H_{18}O_3$: Calculated: M.W.: 258. Found (acidimetry) 260.

EXAMPLE 14

2-[4-(6'-n.octyl-3'-oxo-1'-cyclohexenyl)-phenyl]-propionic acid (Formula V: $R=CH_3$; $R_3=R_4=H$; $R_2=nC_8H_{17}$)

(A). This step is conducted as in Example 13, from ethyl 2-(4-decanoyl-phenyl)-propionate.

(B-C). The hydrochloride of the ester having the formula (II) is treated with sodium ethyl acetoacetate and methyl sulfate, at 0° C., and then at 20° C., and then by refluxing during 6 hours, as in Example 13.

(D). The crude ester of the formula (IV) is saponified as in the preceding examples. The sodium salt is extracted successively with isopropanol and with boiling methylethylketone. The residue is converted to the acid, extracted with ethyl acetate, decolorized over charcoal and isolated as an oil after evaporation of the solvent. Yield: 13%.

Analysis: $C_{23}H_{32}O_3$: Calculated %: C=77.49; H=9.05. Found %: C=77.20; H=9.12.

EXAMPLE 15

2-[4-(2'-n.octyl-3'-oxo-1'-cyclohexenyl)-phenyl]-propionic acid (Formula V: $R=CH_3$; $R_1=R_2=R_3=H$; $R_4=C_8H_{17}$)

(A). This step is conducted according to the procedure used in Example 2.

(B–C). Ethyl 3-oxo-dodecanoate, converted to the sodium derivative by means of sodium ethoxide, is condensed with the ester of the formula (II) described in Example 2. After the usual treatment, the ester of the formula (IV) is obtained as an oil.

(D). The crude ester is dissolved in ethanol and saponified by boiling with a 10% aqueous $Na_2CO_3$ solution, as in the preceding examples. After acidification, extraction with isopropyl oxide and evaporation of the latter, the desired acid is obtained in crystalline form. M.p.=54°–57° C.

Analysis: $C_{23}H_{32}O_3$: Calculated %: C=77.49; H=9.05. Found %: C=77.20; H=9.10.

The derivatives of the formula (X) possess anti-inflammatory and analgesic properties which are therapeutically useful, in particular for the treatment of rheumatic diseases (rheumatoid arthritis, articular rheumatism, spondylarthritis, and the like) and also of local inflammations.

Said properties are evidenced, in particular, by the following conventional pharmacological tests:

(a) Oedema induced by subcutaneous plantar injection, in a rear paw of rats, of a 1% carrageenin solution. The animals are grouped in lots of 7–10 animals and are maintained at 22° C. The reference animals are given a sodium chloride solution, by the oral route. The treated animals are given the test material by the same toute, one hour prior to carrageenin injection. The animals are sacrificed three hours after initiation of the oedema and the protection against the oedema is evaluated by comparison of the volumes of the rear paws in the controls and in the test animals.

(b) Erythema induced by U.V. rays in guinea-pigs after depilation of their dorsilateral area. Irradiation is effected by means of a 500 watt mercury vapour lamp to which the animals are exposed from a distance of 18 cm during two minutes, one hour after administration of the test material. Protection against erythema is evaluated according to an arbitrary scale of from 0 to +++.

(c) Protection against protein denaturation, in vitro (cf. MIZUSHIMA—Arch. Int. Pharmaco. 1964, 149, 1–7 and 1965, 157, 115–124).

(d) KOSTER's analgesia test (Feder. Proceed., 1959, 18, 412) comprising investigating the protective action of the test materials against pain induced in mice by the intraperitoneal injection of acetic acid.

The results obtained are summarized in the following Table.

TABLE

| Product of example | $AD_{40}$ (40% protection) against carrageenin induced oedema | $AD_{50}$ (50% protection) against U.V. | Protection against protein denaturation | Analgesic $AD_{50}$ |
|---|---|---|---|---|
| 1 | 70 mg/kg per os | 50 mg/kg per os | — | 25 mg/kg per os |
| 2 | 1 | 0.7 | — | — |
|   |   |   | ++(= phenyl butazone) |   |
| 4 | 15 | 4 | ++ | 25 mg/kg per os |
| 5 | 15 | — | ++ | — |
| 7 | 0.3 | 0.5 mg/kg per os | ++ | — |
| 9 | 25 | 1.5 | ++ | 30 mg/kg per os |
| 10 | — | 20 | — | — |
| 11 | 2 | 1.2 | ++ |   |

The products of the formula (I) have low toxicity; the lethal dose in rats is comprised, on the average, between 100 and 500 mg/kg per os. They have no action on the central nervous system.

Thus, the invention relates also to a therapeutic composition comprising a derivative of the above-mentioned formula (X), or a pharmaceutically acceptable salt thereof, together with a therapeutically administrable vehicle.

The composition of the invention may be administered:

(a) by the oral route, in the form of tablets, capsules or any other suitable pharmaceutical form, with the usual excipients, the active ingredient being typically in the form of the acid having the formula (X). The administrable dosage is, on the average, from 10 mg to 500 mg active ingredient per day;

(b) in the form of suppositories, at average doses of from 10 mg to 500 mg per day of active ingredient;

(c) in the form of injectable solutions, at a daily rate of from 2 mg to 200 mg active ingredient, particularly in the form of water-soluble salts obtained with non-toxic alkaline or organic bases.

The unit dosage forms of the composition may contain in each unit dose from 1 to 250 mg active ingredient, according to the pharmaceutical formulation selected and the route of administration to be used.

Having now described my invention what I claim as new and desired to secure by Letters Patent is:

1. A compound selected from the group consisting of 4(3-oxo-1-cyclohexenyl) phenyl acetic acid, 2[4(3-oxo-1-cyclohexenyl) phenyl] propionic acid and the pharmaceutically acceptable salts thereof.

2. 4(3-Oxo-1-cyclohexenyl) phenyl acetic acid and the pharmaceutically acceptable salts thereof.

3. 2[4(3-Oxo-1-cyclohexenyl) phenyl] propionic acid and the pharmaceutically acceptable salts thereof.

4. Pharmaceutical compositions having analgesic and anti-inflammatory activity comprising an analgesic and anti-inflammatory effective amount of a compound selected from the group consisting of 4(3-oxo-1-cyclohexenyl) phenyl acetic acid, 2[4(3-oxo-1-cyclohexenyl) phenyl] propionic acid and the pharmaceutically acceptable salts thereof together with a pharmaceutically acceptable carrier.

5. Pharmaceutical composition as claimed in claim 4, in unit dosage form, each unit dosage containing from 1 to 250 mg of said active ingredient.

6. Compounds of the formula:

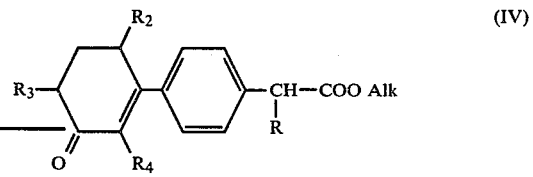

(IV)

in which R, $R_2$, $R_3$ and $R_4$ are selected from the group consisting of hydrogen and the alkyl groups; and their pharmaceutically acceptable salts; the number of carbon atoms in alkyl groups R and $R_3$ being from 1 to 4, and in $R_2$ and $R_4$ being from 1 to 8; Alk being lower alkyl.

* * * * *